(12) United States Patent
Lucas (10) Patent No.: US 7,645,290 B2
(45) Date of Patent: Jan. 12, 2010

(54) MULTI-FUNCTIONAL THROMBECTOMY DEVICE

(76) Inventor: Paul R. Lucas, 10151 Bracken Dr., Ellicott City, MD (US) 21042

( * ) Notice: Subject to any disclaimer, the term of this patent is extended or adjusted under 35 U.S.C. 154(b) by 551 days.

(21) Appl. No.: 11/122,032

(22) Filed: May 5, 2005

(65) Prior Publication Data
US 2006/0253145 A1 Nov. 9, 2006

(51) Int. Cl.
A61B 17/22 (2006.01)
(52) U.S. Cl. .................................. 606/159; 604/22
(58) Field of Classification Search ............ 606/127, 606/128, 113, 159, 167, 169, 170, 171, 180, 606/192, 194, 198, 200; 604/96.01, 158, 604/164.01, 171, 172, 181, 264, 509, 22, 604/19, 523, 533
See application file for complete search history.

(56) References Cited

U.S. PATENT DOCUMENTS

| 4,739,760 | A | * | 4/1988 | Chin et al. ............... 606/159 |
| 4,762,130 | A | | 8/1988 | Fogarty et al. |
| 4,819,634 | A | | 4/1989 | Shiber |
| 4,964,855 | A | * | 10/1990 | Todd et al. ............... 604/533 |
| 4,976,689 | A | * | 12/1990 | Buchbinder et al. ...... 604/95.04 |
| 5,007,896 | A | | 4/1991 | Shiber |
| 5,011,488 | A | | 4/1991 | Ginsburg |
| 5,030,201 | A | | 7/1991 | Palestrant |
| 5,102,415 | A | | 4/1992 | Guenther et al. |
| 5,192,290 | A | | 3/1993 | Hilal |
| 5,376,073 | A | * | 12/1994 | Graves et al. ............ 604/86 |
| 5,417,703 | A | * | 5/1995 | Brown et al. ............ 606/159 |
| 5,474,531 | A | | 12/1995 | Carter |
| 5,501,654 | A | * | 3/1996 | Failla et al. ............ 600/204 |
| 5,501,694 | A | * | 3/1996 | Ressemann et al. ...... 606/159 |
| 5,688,234 | A | * | 11/1997 | Frisbie ................... 604/22 |
| 5,690,606 | A | | 11/1997 | Slotman |
| 5,766,191 | A | * | 6/1998 | Trerotola ................ 606/159 |
| 5,772,674 | A | | 6/1998 | Nakhjavan |
| 5,827,229 | A | | 10/1998 | Auth et al. |
| 5,833,644 | A | * | 11/1998 | Zadno-Azizi et al. ...... 604/509 |
| 5,928,218 | A | | 7/1999 | Gelbfish |
| 6,022,309 | A | | 2/2000 | Celliers et al. |

(Continued)

OTHER PUBLICATIONS

ProLumen™ Rotational Thrombectomy System, Product Brochure, Datascope Interventional Products, P/N:0002-08-10137.

(Continued)

*Primary Examiner*—Anhtuan T Nguyen
*Assistant Examiner*—Jocelin C Tanner
(74) *Attorney, Agent, or Firm*—Rosenberg, Klein & Lee (57) ABSTRACT

A hand held motor powered device for percutaneous thrombolysis and evacuation of a clot from a clotted arterio-venous fistula is disclosed. The percutaneous thrombectomy device is provided with a plurality of nested coaxial lubricious catheters. The multi-functional thrombectomy device can simultaneously and sequentially degrade and evacuate a blood clot from a blood vessel by multiple modalities that combines to degrade the clot by mechanical agitation, fragmentation and disruption, by peri-thrombus delivery of enzymatic fluids, by irrigation with biocompatible fluids, and by balloon displacement. The thrombectomy device further provides for balloon containment and isolation of clot debris from the general circulation, thereby minimizing the risks to a patient of embolic sequelae. There is also provided an optional steering mechanism for controlled deflection of the working end of the device.

18 Claims, 5 Drawing Sheets

U.S. PATENT DOCUMENTS

| | | | |
|---|---|---|---|
| 6,027,514 A | 2/2000 | Stine et al. | |
| 6,206,900 B1 | 3/2001 | Tabatabaei et al. | |
| 6,258,108 B1 * | 7/2001 | Lary | 606/159 |
| 6,263,224 B1 | 7/2001 | West | |
| 6,454,775 B1 * | 9/2002 | Demarais et al. | 606/128 |
| 6,514,191 B1 | 2/2003 | Popowski et al. | |
| 6,530,935 B2 | 3/2003 | Wensel et al. | |
| 6,602,264 B1 * | 8/2003 | McGuckin, Jr. | 606/159 |
| 6,605,074 B2 * | 8/2003 | Zadno-Azizi et al. | 604/509 |
| 6,652,548 B2 | 11/2003 | Evans et al. | |
| 6,660,014 B2 | 12/2003 | Demarais et al. | |
| 6,663,613 B1 | 12/2003 | Evans et al. | |
| 6,818,002 B2 | 11/2004 | Shiber | |
| 6,932,829 B2 * | 8/2005 | Majercak | 606/198 |
| 2002/0010487 A1 | 1/2002 | Evans et al. | |
| 2002/0032455 A1 | 3/2002 | Boock et al. | |
| 2002/0198491 A1 | 12/2002 | Miller et al. | |
| 2003/0171741 A1 | 9/2003 | Ziebol et al. | |
| 2003/0195536 A1 * | 10/2003 | Bashiri et al. | 606/159 |
| 2004/0082962 A1 | 4/2004 | Demarais et al. | |
| 2004/0097880 A1 | 5/2004 | Schur | |
| 2005/0021013 A1 | 1/2005 | Visuri et al. | |

OTHER PUBLICATIONS

Arrow, Arrow-Trerotola Over-The Wire (OTW) PTD (Percutaneous Thrombolytic Device) Catheter Product to be used with Arrow OTW Rotator Drive Unit, Product Manual, Arrow International, T-65609-101E, Rev. 1 (Jul. 2004).

* cited by examiner

MULTI-FUNCTIONAL THROMBECTOMY DEVICE

FIELD OF THE INVENTION

The subject invention relates to a medical device for lysis and evacuation of a clot within a blood vessel. In particular, the present invention is directed to a device for percutaneous thrombectomy, i.e. the thrombolysis and evacuation of an intravascular thrombus in a living mammal. Even more particularly, the present invention directs itself to a medical device for percutaneous thrombolysis and evacuation of clot from a clotted arterio-venous fistula.

Furthermore, the subject invention is directed to a percutaneous device for clot thrombectomy by a number of simultaneous and sequential modalities, comprising a plurality of displaceable and coaxial catheter members for mechanical agitation, fragmentation and disruption of a thrombus; for peri-thrombus infusion of and irrigation with biocompatible fluids; for peri-thrombus delivery of pharmacologic agents; and for displacement and evacuation of an intravascular clot with at least one reversibly inflatable balloon-like member important for the containment of clot fragments and debris and their subsequent controlled removal from the vascular system.

Additionally, the present invention relates to a hand-held medical thrombectomy device for percutaneous placement of a catheter assembly comprising at least one balloon catheter member; a guidewire; an optionally steerable tined catheter having a plurality of radially displaceable and rotatable resilient tines coupled to an electrically or hydraulically powered motor unit 200 housed within the handle and activated with an actuating mechanism; and further provided with at least a pair of irrigation catheters, assembled for the mechanical and/or enzymatic lysis of a clot within a blood vessel and/or arterio-venous ("AV") fistula and/or vascular graft, containment of clot debris by the inflated balloon(s), and subsequent irrigation and removal of macroscopic and microscopic clot debris from the vascular compartment.

With further particularity, the subject invention directs itself to a hand-held percutaneous thrombectomy device having a plurality of respectively displaceable coaxial catheter members, and further provided with an actuating handle unit allowing the simultaneous and/or sequential activation of the subject invention's available thrombolytic modalities, including but not limited to clot disruption by mechanical shearing and maceration; mechanical fluid agitation from expansible rotatory actions of expandable and resilient distal catheter tines; peri-thrombus delivery of thrombolytic pharmacologic agents; and clot capture and controlled displacement using at least one slidably displaceable inflatable catheter member.

BACKGROUND OF THE INVENTION

Patients with end-stage renal disease, regardless of etiology, require hemodialysis several times a week as an absolute medical necessity. Furthermore, such dialysis-dependent patients have chronic pulmonary compromise due to ventilation perfusion mismatching. Consequently, end stage renal patients have an increased susceptibility to further pulmonary insults, which may include the accumulated micro-thrombi that can shower the pulmonary microvasculature as micro-emboli during relatively uncontrolled thrombolytic and thrombectomy interventions.

Hemodialysis necessarily, inherently requires a reliable vascular access supplied with a robust blood flow that can support the associated large fluid and blood volume shifts. In order to provide adequate vascular access, an AV fistula is surgically created by anastamosing a peripheral artery and vein, typically in an arm or leg. The turbulent blood flow within an AV fistula creates areas of relative blood stasis which thereby predispose to thrombus formation and clot growth that often further leads to occlusion of the vascular lumen. Clotted AV fistulae are relatively common, and necessitate surgical clot removal, or synonymously, thrombectomy to salvage the AV fistula vascular access; if the clot is too extensive, it becomes necessary to tie off, which is to say, ligate, the clotted AV fistula and create a new one at another anatomic site.

Furthermore, AV fistula thrombectomies are done in an Operating Room since currently available techniques involve either open dissection with arteriotomy access to the clot, or closed techniques with the associated increased risks of uncontrolled hemorrhage, both situations requiring the concentrated resources available in an operating room.

It is a goal of the present invention to provide a medical thrombectomy device that can safely be used outside the operating room, whether in a facility x-ray suite or dialysis unit, in a procedure room or bedside.

It is also a goal of the subject invention to provide for optimal thrombectomy by the combined effects of mechanical agitation and shearing and balloon displacement with peri-thrombus delivery of pharmacologic agents.

It is an important objective of the present invention to minimize the size of the access puncture into the blood vessel in order to insert the thrombectomy devices' nested coaxial catheters.

PRIOR ART

Thrombectomy devices are well known in the prior art. For example, patent application publication US 2002/0010487 is directed to expansible shearing catheters for thrombus removal, providing for expansible baskets comprised of helically oriented independently flexible struts that function as cooperating radially expansible shearing members. The inner basket may be rotatably driven and may use an axial pump extending proximally from the shearing members.

U.S. Pat. No. 5,928,218 teaches a minimally invasive assembly that comprises a tubular member with a large-diameter distal end portion and a smaller diameter proximal portion, a clot-intake port at the distal end and a cutter element that is movably disposed in the distal end of this tubular device for cutting or macerating or severing material that is sucked into the intake port. The device assembly further encompasses a balloon at the distal end of the tubular member that is inflated with irrigation fluid controlled by a valve that operationally responds to the position of the cutter element.

U.S. Pat. No. 5,102,415 is directed to an apparatus for removing blood clots from arteries and veins, a triple catheter with an outer catheter that can be inserted into a blood vessel; an inner catheter with an inflated balloon at its distal end. The intermediate catheter is radially expandable at its distal end with a receptacle that is an elastic mesh structure made of spring wires or similar plastic monofilaments. By utilizing a self-expanding basket or end receptacle mounted on the intermediate catheter, the basket is supposed to drag along the walls of the vessel and be able to clear away the thrombus without leaving any clot portions in the blood vessel.

U.S. Pat. No. 6,663,613 uses an "agitator" to effect clot dissolution in addition to introducing a thrombolytic agent within the clot. The mechanical agitation itself breaks up the clot to some extent and the addition of a thrombolytic agent aids with the dispersal of that pharmacologic substance and a synergistic effect for clot disruption. The mechanical agitation means on the catheter body may be a radially expansible agitator that is rotatable and/or axially translatable relative to the catheter body. Alternatively, the radially expansible agitator may comprise a resilient element which can be axially shortened so as to assume an enlarged profile and then straightened and so on. By cycling the expansible agitator element through straightening and arching by axial shortening, mechanical energy is translated into breaking up the clot. U.S. Pat. No. 6,652,548 is a similar device of the same inventors, with distal balloon tipped catheter containment of the thrombus as well as proximal balloon catheter containment, coupled with a thrombus removal catheter.

U.S. Pat. No. 4,762,130 discloses and claims a thrombectomy catheter with a radially expansible corkscrew-like balloon at the tip of a percutaneously placed catheter. The distal end of the catheter is advanced at least partly through the thrombus with the balloon in a contracted or deflated condition and once in position, the corkscrew-like balloon is inflated, thereby expanding into its helical configuration so as to engage the clot. The helical balloon at the catheter tip has sealing loops permitting the flow of blood within the vessel in order to propel the catheter along inside the vessel. The catheter is further provided with a plurality of lumens that allow injection of diagnostic and thrombolytic agents, etc. The inflation of the radially expansible helical balloon is done with the catheter tip just past the thrombus so that the expanding helix lies within the blood clot; withdrawing the catheter is then akin to withdrawing a cork from a wine bottle.

There exists a need for a medical device to accomplish a thrombectomy that is percutaneously placed, encompasses thrombolysis by the concurrent and sequential application of mechanical agitation, shearing, fragmentation, maceration and cutting, pharmacologic degradation of the clot, balloon containment of clot debris, balloon displacement of clot to an evacuation port, irrigation of the area around the clot with saline or other biocompatible fluid, and which further allows substantially one-handed deployment and operation of these thrombectomy modalities.

DETAILED DESCRIPTION OF THE PREFERRED EMBODIMENT

Figure 1:
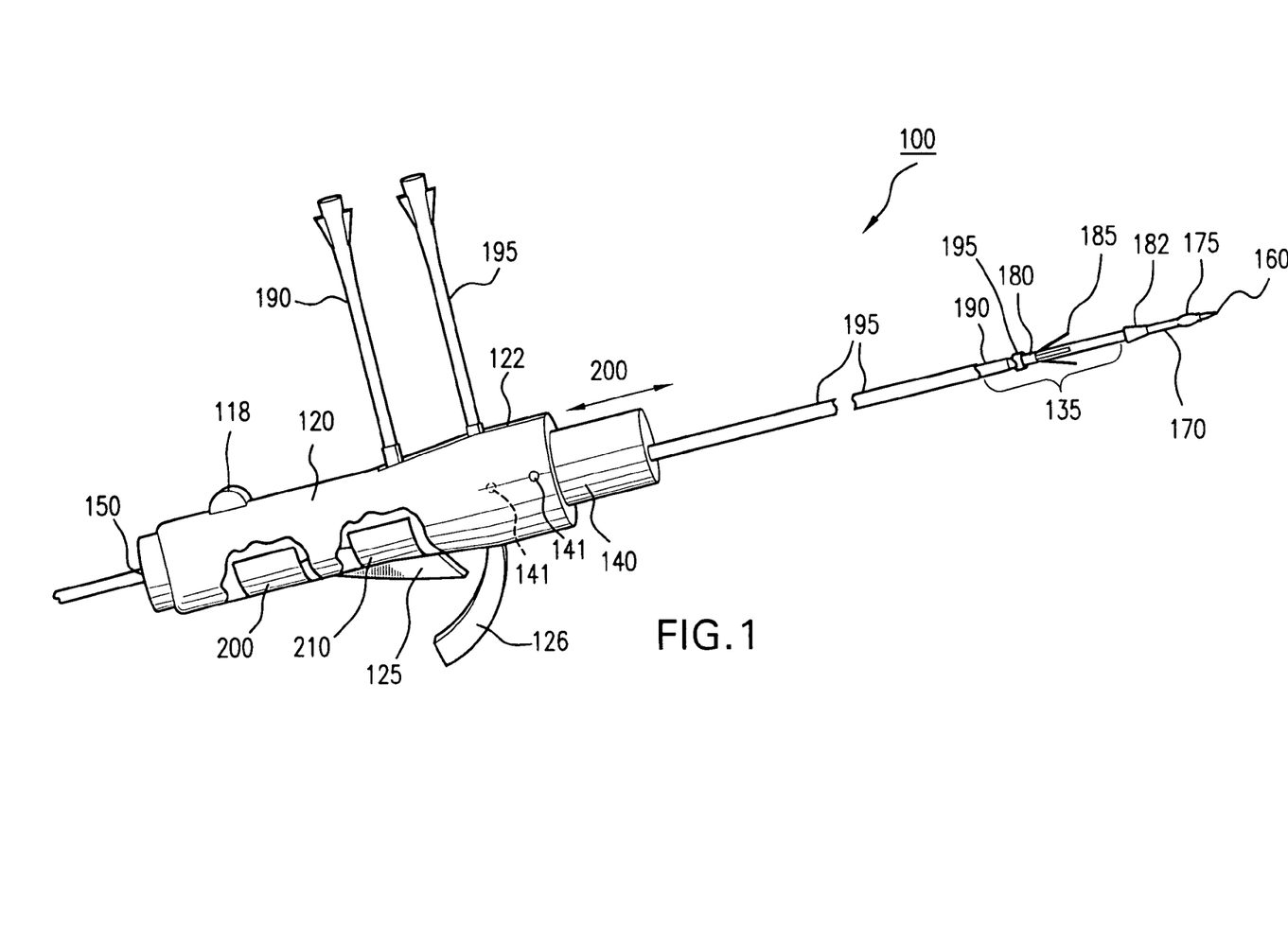
FIG. 1 is a perspective view of the percutaneous thrombolysis device in the deployed condition.

The details of the percutaneous thrombectomy device 100 may be best appreciated with reference to the Figures. FIG. 1 illustrates the medical thrombectomy device 100 in perspective view, showing the device 100 in a deployed operable condition. At the proximal end, 'proximal' being understood to signify the direction toward the handle and the device operator, a handle housing 120 is seen with the telescoping displaceable control housing 140 in a partially retracted position having the tines 185 partially exposed and radially expanded. The irrigation catheters 190, 195, which consist of both an infusion catheter 190 and an evacuation catheter 195, are fixedly connected or attached to control housing 140 through which they pass.

Protruding longitudinally away from the handle housing 120 is a control housing 140, a hollow semi-rigid displaceable cylindrical extension in which a plurality of catheter members are slideably contained. Catheters 190, 195 are fixedly connected to control housing 140 so as to move together as a unit upon longitudinal displacement 200 for the deployment, or un-deployment, of the functional distal end of the device 100. The irrigation catheters 190, 195 fixedly attached to control housing 140, are slidingly received into a recess 122 formed in the handle housing 120, the recess having a length substantially equal to distance 135 of catheter-190's longitudinal excursion between operable and protected conditions.

Figure 7:
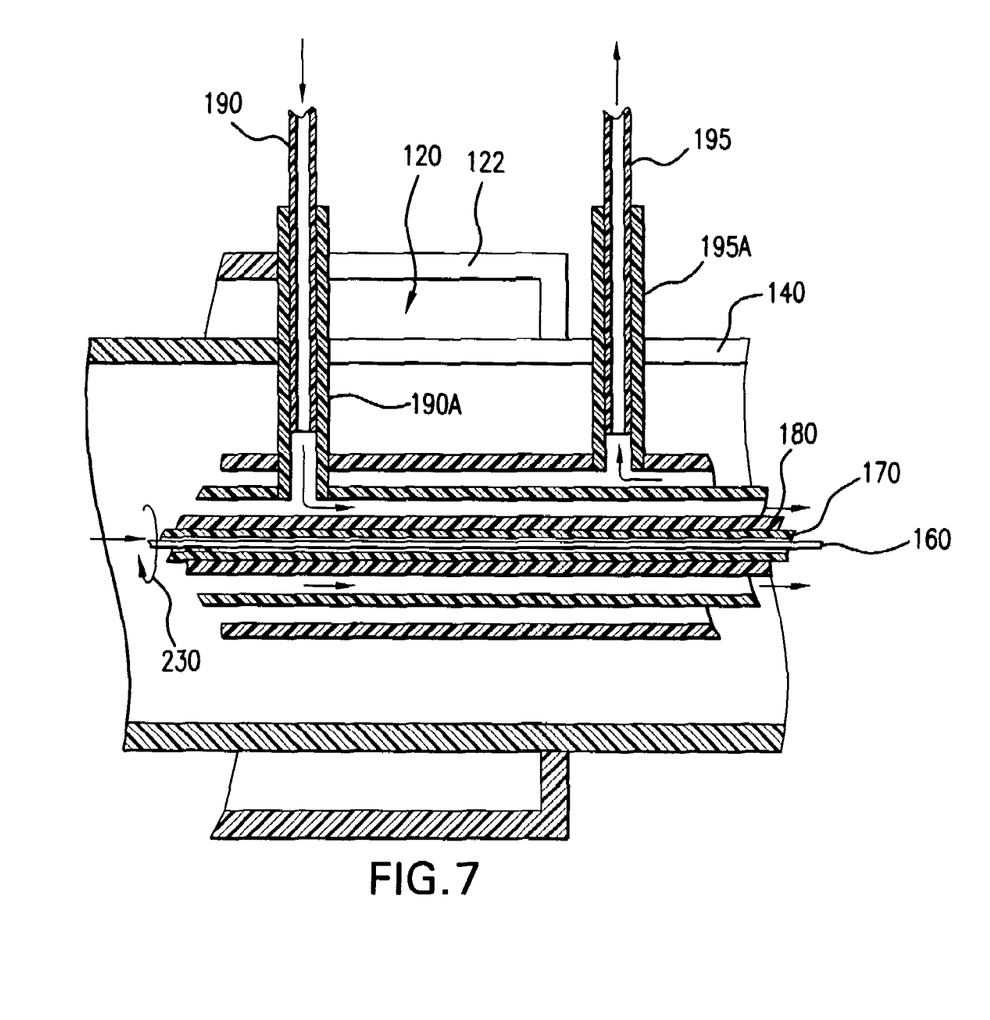

The plurality of coaxially positioned catheters comprises an evacuation catheter 195 coaxially positioned around an infusion catheter 190, with each of the catheters secured to the control housing proximally. The catheters extend through the control housing 140 and terminate proximally with a catheter connector formed at a proximal opening of each catheter 190. 195. As illustrated in FIG. 7, the proximal ends of the irrigation catheters 190, 195 exit from the control housing and are connectable to any standard fluid conduit such as IV tubing, irrigation syringes and so on. The catheters have an opening, also referred to as a fenestration, formed in the outer surfaces of the catheters at a location in line with the through conduit 150. These fenestrations are hermetically sealed with an elastomeric member having a self-sealing aperture centrally positioned: these are often referred to as diaphragms and they allow a guidewire 160 and a balloon catheter 170 to be passed through the self-sealing central opening in the diaphragm and be advanced into the catheter lumens while maintaining a fluid-tight seal.

Activation mechanism 125 is depicted mounted in handle housing 120 and allows an operator to start the thrombectomy device motor 200 housed in the handle 120, which in turn rotates tines 185 along with catheter 180 from which the tines 185 are formed. The motor 200 is preferably powered by a battery 210 housed within the handle housing 120 but power may alternatively be supplied by an external source including electrical, mechanical and pressurized fluid sources. Further appreciated in FIG. 1 is the arcuately elongate shaped displacing guard 126 which is pivotally displaceable from a closed position in which it blocks inadvertent activation of activation mechanism 125, to a more distal forward open position allowing activating access to activation mechanism 125. Displacing guard 126 is thus pivotally displaceable forward and away from the blocking position to an un-blocking position, as illustrated, that allows access to activation mechanism 125. The displacing guard is constrained in its pivotal displacement from contacting or activating the activation mechanism 125. Importantly, the pivotal displacement of the guard 126 simultaneously controls the longitudinal displacement 200 of control housing 140 and catheters 190, 195 attached thereto. The functional effect is that displacing guard 126, which is connected to control housing 140 within housing 120, longitudinally displaces the telescopically displaceable catheter assembly 140, 190, 195 from a operable condition to a protected condition and vice versa.

The telescoping displacement of the catheters 190, 195—longitudinally 200 in a distal direction to form a sheath to cover tines 185 when in the protected condition, and in a proximal direction to an operable or retracted condition with tines 185 unsheathed—incorporates a locking mechanism. The preferred locking mechanism is illustrated as a detent locking mechanism 141 comprising a plurality of reversibly engaging detent locking members. Other locking member embodiments include—but are not limited to—a sliding bolt action; a latch mechanism; and so on. Such locking members as are functionally equivalent are within the contemplation and scope of the present subject invention.

Spring biased detent balls engage respective detent recesses formed in corresponding surfaces of handle housing 120 and control housing 140 respectively. While it is preferred that spring biased detent balls be formed in the handle housing 140 and the respective detent recesses 141 formed in the outer surface of control housing 120, it is equivalent for the recesses to be formed in the handle housing 120 and the matching detent balls formed in the respective control housing 140. The recesses are situated to reversibly secure the control housing in the handle housing both in the operable and in the protected conditions. The device reversibly locks the respective position of the control housing 140 and handle housing 120, with both the protected condition and also the operable or retracted condition effected upon the pivotal displacement of a displacing guard 126 connected to control housing 140. In the preferred embodiment it is the displacing guard which is used to cause the longitudinal displacement of control housing 140 with respect to handle housing 120.

The device 100 is in an operable condition when control housing 140 is longitudinally displaced proximally to a reversibly complementary juxtaposition with the handle housing 120, which thereby uncovers tines 185, allowing the tines 185 to expand radially.

Additionally, as seen illustrated in FIG. 1 there is optionally provided a control wheel 118 that is steerably connected to the fusiform tip 182 of catheter 175 thereby providing controlled displaceability to the working end of the device 100.

Coaxial and interior to the evacuation catheter 195 is an infusion catheter 190; coaxial and interior to both the irrigation catheters 190, 195 is a tined catheter 180. Tined catheter 180 has formed at its distal aspect a plurality of resilient radially expandable finger-like tines 185 that are allowed to expand radially upon the proximal longitudinal displacement 200 of control handle 140 together with evacuation catheter 195 and infusion catheter 190. Tined catheter is not longitudinally displaceable with respect to the handle housing 120 and is secured in the longitudinal axis by its connection with the motor 200 gearing (or similar frictional engagement members) and/or other anchoring means well known to those skilled in the art of medical devices.

Also illustrated in FIG. 1 the balloon tip catheter 170 is positioned interior to and coaxial with the other catheters 180, 190, 195, and is formed with a valved reversibly inflatable member at its distal end proximal to the radially expandable tines 185, a fusiform member 182 of the balloon catheter 170 is formed. Guidewire 160 is advanced along the through conduit 150 positioned longitudinally through the thrombolysis device 100; the guidewire 160 occupies a central, axial position relative to the nested coaxial catheters 170, 180, 190, and 195. The distance 135, from the proximal end of the fusiform member 182 to the distal opening of evacuation catheter 195 is the telescoping distance, the maximal extent of longitudinal displacement for the control handle 140 having the irrigation catheters 190, 195 attached. The displacement proximally along direction 200 which is to say the excursion of the fixed irrigation catheters 190, 195 into handle recess 122 is substantially the same distance as the telescoping distance 135.

Figure 2:
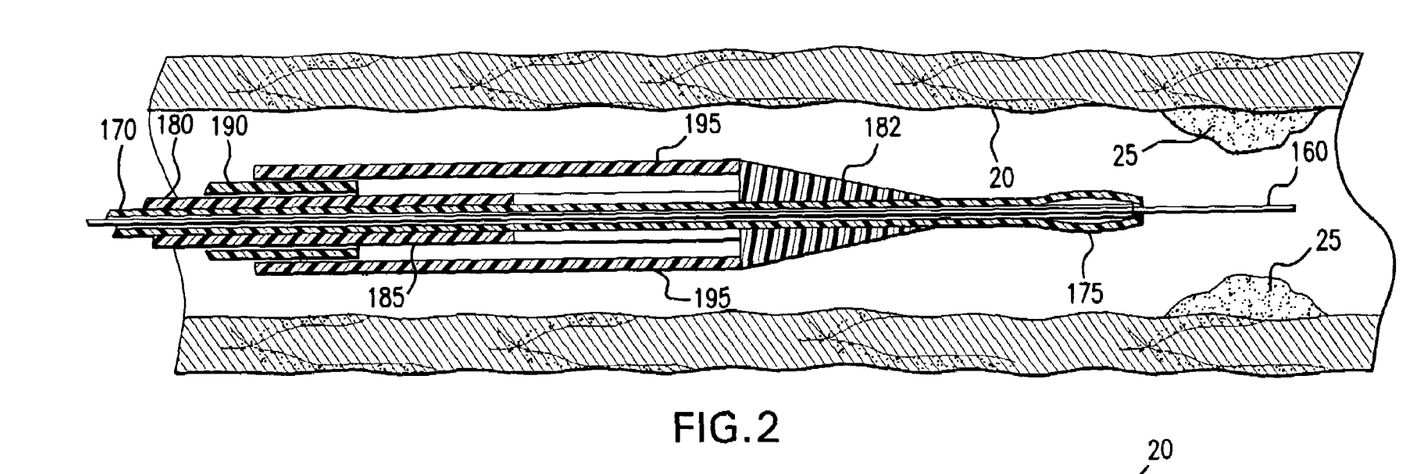
FIG. 2 is a cross-sectional side view of the undeployed device positioned with a guidewire advanced to the level of a clot in a blood vessel.
Figure 3:
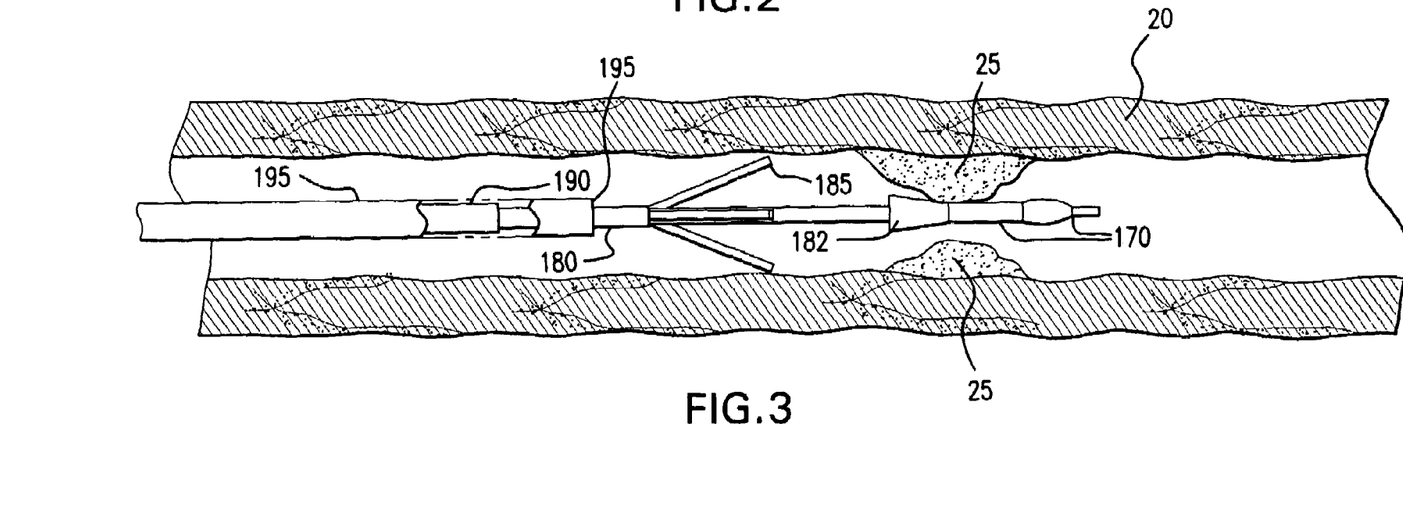
FIG. 3 is a cross-sectional side view of the device having the tines deployed, the device being positioned with a balloon tipped catheter proximal to a clot in a blood vessel.
Figure 4:
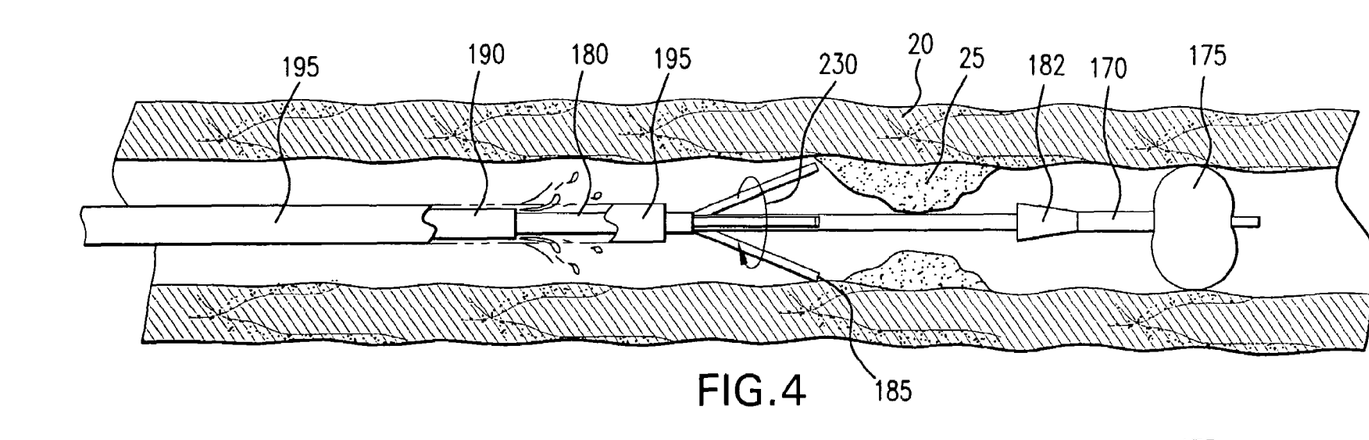
FIG. 4 is a cross-sectional side view of the device having the deployed tines rotating and further having an inflated balloon member positioned proximal to a clot in a blood vessel.
Figure 5:
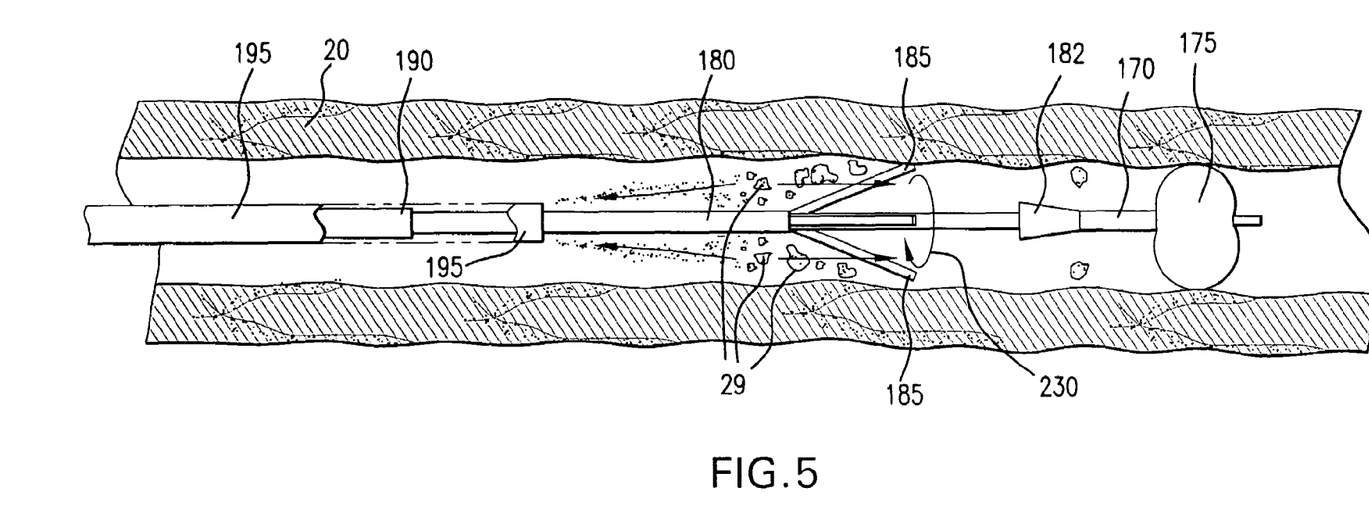
FIG. 5 is a cross-sectional side view of the device in the deployed condition.
Figure 6:
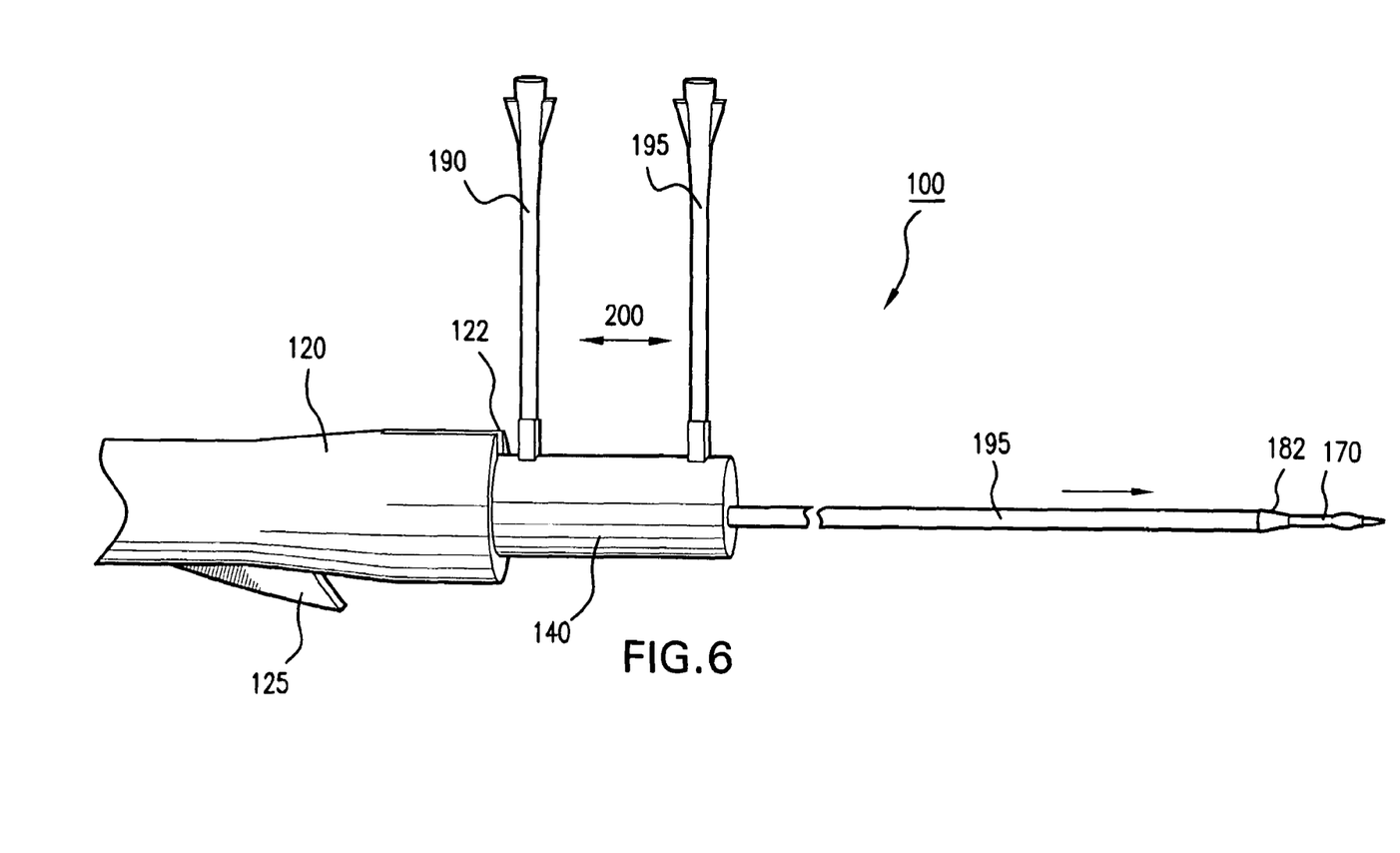
FIG. 6 is a side-view of the thrombolysis device in the undeployed condition; and, FIG. 7 is a functional cross-sectional side view showing the respective catheter members of the medical percutaneous thrombectomy device.

As seen in greater detail in FIG. 2 and in subsequent FIGS. 3-5, the plurality of nested telescoping coaxial catheters, seen here positioned within the lumen of a blood vessel 20 with guidewire 160 advanced to the level of a thrombus or clot 25. In operation, guidewire 160 is first advanced percutaneously into the blood vessel with a clot; the through conduit 150 of the medical device 100 provides a hollow channel into which to insert an end of guidewire 160; the medical device 100 is then passed over the guidewire 160 into position near the clot.

In order to facilitate the atraumatic positioning of the nested coaxial catheters, tined catheter 180 is fitted at its distal end with a fusiform or cone-like member 182 that has a maximal outside diameter at its base substantially equal to the outside diameter of the juxtaposing catheter 195. This smooth profile of the catheter when in the closed conformation serves to minimize the risk of traumatic abrasion or puncture or other damage to the blood vessel and/or surrounding tissues during placement. The device as seen in FIG. 2 is in the undeployed condition. By this is meant the condition in which the irrigation catheters 190, 195 are positioned as far distally as possible so that the distal tip of the evacuation catheter 195 is juxtaposed with the base of the cone-like member 182 forming thereby a relative smooth surface. The expandable tines 185 are reversibly deformed to a collapsed or contracted state, held in that position by the sheath formed by the irrigation catheters 190, 195.

All of the catheters 180, 190, 195 and the guidewire 160 are optionally and preferably provided with a lubricious coating so as to facilitate the working of device 100.

The fusiform catheter tip 182 represents the distal terminal aspect of tined catheter 180. A steering mechanism optionally attaches to the fusiform catheter tip 182 so as to provide controlled deflectability; the mechanism may be any of the deflecting mechanisms well known to those practiced in the art of medical devices. For example, steering tendons in the form of wires may be used to cause the desired controlled deflection of the functioning end of device 100.

Once the working end of the thrombolysis device 100 is positioned close to the blood clot 25 as seen in FIG. 3, the irrigation catheters 190, 195 are longitudinally displaced in a proximal direction, thereby disinhibiting the compressed and/or folded expandable tines 185 and allowing them to radially expand. In addition, a balloon-tipped catheter 170 is advanced over the guidewire through the lumen of tined catheter 180 and advanced distally so that the reversibly expandable balloon member 175 comes to rest in a position proximal to the thrombus 25. The expandable tines 185 displace radially as far as the internal dimensions of the blood vessel 20 permit. Balloon catheter 170 is optionally provided with a second reversibly expandable balloon member located on the opposite side of the tines 185, for further vascular containment of clot debris 29. All reversibly expandable balloon members have valves formed proximally in line with the catheter lumens so as to permit controlled inflation and deflation with a fluid under pressure. In the preferred embodiment the preferred fluid is physiologic saline, a 0.9 Normal aqueous solution of sodium chloride. Other biocompatible crystalloids or colloid liquids are likewise preferred. Not shown is the proximal connection of tined catheter 180 to the motor 200; rotations of the motor 200 are transferred to the tined catheter causing the tined catheter 180 and the tines 185 formed at its distal aspect to rotate upon activation of the motor 200 by activation, member 125. The rotational connection is effected preferably by a set of gears or similar engaging members that frictionally transfer the motor's 200 rotations to the tined catheter 180 causing it to rotate.

FIG. 4 shows the next step in the thrombectomy method of the present invention, illustrating the delivery of a biocompatible fluid through infusion catheter 190. Further illustrated is the radially rotatory displacement of tines 185 in a preferred clockwise movement, allowing tines 185 to degrade the clot 25 by macerating, cutting, shearing and mechanical agitation and displacement. Further seen in FIG. 4 is balloon 175 in the inflated condition. The inflation of balloon 175 at a position proximal to the clot 25 is important for isolating and containing the clot debris 29 resulting from mechanical disruption, lysis and pharmacologic degradation of the clot 25. The evacuation of the clot debris 29 and the fluid and blood in which it is carried is seen illustrated in FIG. 5 as the debris 29 is suctioned into evacuation catheter 195.

FIG. 5 further shows the thrombectomy device 100 having the balloon member 175 inflated with the tines 185 deployed and rotatingly displaced, also positioned with the inflated balloon tipped catheter 170 situated proximal to a clot 25 in a blood vessel 20, illustrating the evacuation of debris 29, the direction of rotation of the tines 185, and the spread of some thrombus material 29 near the containment balloon 175. FIG. 5 illustrates how some debris 29 having migrated proximally, which is to say away from the inserted device 100, may be contained by the inflated balloon 175 to thereby prevent such debris 29 from entering the general circulation with the associated risks of micro emboli and thrombus formations.

The functional relationship of the plurality of nested catheters of the thrombectomy device 100 is illustrated in FIG. 7. Fluid infusates, with or without pharmacologic agents such as enzymes and other degradative biochemical agents, are introduced through catheter 190. Catheter 190 has a rigid section 190A fixedly attached to handle housing 120 and joining flexible sections of catheter 190 both proximally and distally. The connection between the flexible sections of 190 and the rigid section 190A is accomplished by a hermetic locking mechanism, such as a Luer lock or other similar mechanism. Fluid entering the infusion catheter 190 is directed toward the working end of the device. The infusion catheter is seen to surround the tined catheter 180 which further surrounds balloon tip catheter 170, still further having guidewire 160 centrally located; the longitudinal sections of all of the catheters are coaxial as schematically illustrated in FIG. 7. Fluid is evacuated through catheter 195, the outermost catheter in the nested catheters of the device 100, as a result of suction or some other differential pressure creating mechanism. The preferred direction of rotation 230 taken by the tined catheter 180 is indicated; tined catheter 180 has connected at its distal end the plurality of radially expandable tines 185 formed therefrom.

Although this invention has been described in connection with specific forms and embodiments thereof, it should be appreciated that various modifications other than those discussed above may be resorted to without departing from the spirit or scope of the invention. For example, equivalent elements may be substituted for those specifically shown and described, certain features may be used independently of other features, and in certain cases, particular locations of elements may be reversed or interposed, all without departing from the spirit or scope of the invention as defined in the appended claims.

I claim:

1. A medical percutaneous thrombectomy device for removal of a clot from a blood vessel, comprising:
   (a) a handle housing having a through conduit longitudinally formed therein for slidingly receiving therethrough a guidewire and provided with an actuating mechanism fixedly located through a surface of said handle housing;
   (b) a control housing protruding from and slidably positioned within said handle housing, having a pair of irrigation catheters mounted to said control housing being linearly displaceable within a recess formed through a wall of said handle housing, and adapted for longitudinal displacement relative to said handle housing;
   (c) a tined catheter having a balloon catheter extending therethrough, said tined catheter having a plurality of tines and a fusiform tip member fixedly mounted thereto and contiguous a distal end of an evacuation catheter when said medical percutaneous thrombectomy device is in an undeployed state wherein said plurality of tines are contained within said evacuation catheter and displaced from said distal end of evacuation catheter when said medical percutaneous thrombectomy device is in a deployed state, said fusiform tip member having a base diameter substantially equal to an outer diameter of said evacuation catheter in said undeployed state, said tined catheter being longitudinally secured and undisplaceable relative to said handle housing and rotatably seated within said through conduit, distally protruding through said handle housing and said control housing, being rotationally coupled at a proximal end to a motor housed in said handle housing; and,
   (d) a plurality of coaxially positioned catheters positioned over said balloon catheter through said control housing, said coaxially positioned catheters including said evacuation catheter, an infusion catheter, and said tined catheter,
   wherein said balloon catheter has a balloon mounted on a distal end of said balloon catheter, at least one of said catheters having at least one of a plurality of thrombectomy modalities, providing for fragmentation of said clot wherein said balloon is positioned distal to said clot for preventing fragments of said clot from being displaced distal to said balloon within said blood vessel; and
   wherein said evacuation catheter and said infusion catheter are slidably positioned over said tined catheter and said balloon catheter.

2. The medical percutaneous thrombectomy device for removal of a clot from a blood vessel as recited in claim 1 with said plurality of thrombectomy modalities further comprising a fragmentation mechanism including said plurality of tines for mechanical agitation, shearing, and disruption of a clot within a vascular structure.

3. The medical percutaneous thrombectomy device for removal of a clot from a blood vessel as recited in claim 1, with said plurality of thrombectomy modalities includes at least one reversibly inflatable member defining said balloon for isolating a plurality of clot fragments of said clot from entering a vascular circulation wherein one of said irrigation catheters is provided with an infusion port to infuse a biocompatible fluid in an effective proximity to said clot, and an evacuation port to remove said fluid with said plurality of clot fragments contained therein.

4. The medical percutaneous thrombectomy device for removal of a clot from a blood vessel as recited in claim 1 wherein said guidewire has a length greater than a longitudinal length of said thrombolytic device, said guidewire being external to said device and inserted into and through said through conduit, said through conduit being positioned coaxially central to a plurality of successive longitudinal segments of the respective plurality of coaxially positioned catheters.

5. The medical percutaneous thrombectomy device for removal of a clot from a blood vessel as recited in claim 1 wherein said balloon catheter is positioned within said catheters and surrounding said guidewire having said balloon secured thereon and further provided proximally with at least one inflation port with a valve for reversibly filling said balloon with a fluid under pressure.

6. The medical percutaneous thrombectomy device for removal of a clot from a blood vessel as recited in claim 4 having a balloon catheter length substantially equal to said guidewire length.

7. The medical percutaneous thrombectomy device for removal of a clot from a blood vessel as recited in claim 2, wherein said fragmentation mechanism comprises said plurality of tines that are radially expandable and resilient, formed on a distal end of said tine catheter.

8. The medical percutaneous thrombectomy device for removal of a clot from a blood vessel as recited in claim 3, wherein said biocompatible fluid comprises at least one active species for biochemically degrading said clot.

9. The medical percutaneous thrombectomy device for removal of a clot from a blood vessel as recited in claim 3, wherein said biocompatible fluid comprises at least one active species for enzymatically degrading said clot.

10. The medical percutaneous thrombectomy device for removal of a clot from a blood vessel as recited in claim 7, having a deployed condition and an undeployed condition, wherein said device is in the deployed condition when said control housing is longitudinally displaced proximally to a reversibly complementary juxtaposition with said handle housing thereby reversibly uncovering said plurality of tines and allowing said plurality of tines to expand radially.

11. The medical percutaneous thrombectomy device for removal of a clot from a blood vessel as recited in claim 10 wherein a change is effected between a deployed condition and an undeployed condition by a displacing guard member pivotally attached to said handle housing, wherein said displacing guard member has a closed position for obstructing an access to an activation member, and upon pivotal displacement assumes an open position that allows access to said activation member, said displacement guard being attached to said control housing so as to effect a longitudinal displacement with respect to said handle housing.

12. The medical percutaneous thrombectomy device for removal of a clot from a blood vessel as recited in claim 1, further comprising a control wheel rotatably mounted on said handle housing and connected to said fusiform tip member formed on a distal end of said tined catheter, wherein rotation of said control wheel causes a responsive displacement of said plurality of coaxially positioned catheters.

13. The medical percutaneous thrombectomy device for removal of a clot from a blood vessel as recited in claim 2 wherein said fragmentation mechanism comprises at least three tines formed at regular intervals on a distal end of said tined catheter.

14. The medical percutaneous thrombectomy device for removal of a clot from a blood vessel as recited in claim 1 wherein said plurality of coaxially positioned catheters comprises said infusion catheter coaxially positioned around said evacuation catheter, each of said catheters proximally fixed to said control housing and extending therethrough and terminating proximally with a catheter connector formed at a proximal opening of each of said catheters to reversibly couple said catheters to a plurality of standard fluid conduits, said catheters further including an opening formed in a catheter outer surface located in longitudinal alignment with said through conduit and hermetically sealed with an elastomeric member having a self-sealing aperture centrally positioned and adapted to accept therethrough said guidewire and said balloon catheter and maintain a fluid-tight seal.

15. The medical percutaneous thrombectomy device for removal of a clot from a blood vessel as recited in claim 14 wherein each of said plurality of coaxially positioned catheters is provided with a lubricious coating.

16. The medical percutaneous thrombectomy device for removal of a clot from a blood vessel as recited in claim 1 wherein said tined catheter is provided with a lubricious coating.

17. The medical percutaneous thrombectomy device for removal of a clot from a blood vessel as recited in claim 1 wherein a motor is electrically connected to a battery housed within said handle housing and actuated by said actuating member.

18. The medical percutaneous thrombectomy device for removal of a clot from a blood vessel as recited in claim 17 wherein said motor is powered by an external power source and actuated by said actuating member.

* * * * *

UNITED STATES PATENT AND TRADEMARK OFFICE
CERTIFICATE OF CORRECTION

PATENT NO. : 7,645,290 B2  
APPLICATION NO. : 11/122032  
DATED : January 12, 2010  
INVENTOR(S) : Paul R. Lucas It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 841 days.

Signed and Sealed this

Twenty-first Day of December, 2010

David J. Kappos
*Director of the United States Patent and Trademark Office*